(12) United States Patent
Griffin, III et al.

(10) Patent No.: US 6,440,488 B2
(45) Date of Patent: Aug. 27, 2002

(54) FLEXIBLE ELECTRODE CATHETER AND PROCESS FOR MANUFACTURING THE SAME

(75) Inventors: Joseph C. Griffin, III, Atco, NJ (US); Anthony Abbate, Novato, CA (US)

(73) Assignee: EP MedSystems, Inc., West Berlin, NJ (US)

(*) Notice: Subject to any disclaimer, the term of this patent is extended or adjusted under 35 U.S.C. 154(b) by 63 days.

(21) Appl. No.: 09/729,649

(22) Filed: Dec. 4, 2000

Related U.S. Application Data

(60) Provisional application No. 60/168,905, filed on Dec. 3, 1999.

(51) Int. Cl.$^7$ .................................................. A61N 1/05
(52) U.S. Cl. ..................... 427/2.3; 427/2.11; 607/116; 607/122
(58) Field of Search .................... 607/122, 116, 607/115, 119; 427/2.3, 2.11, 2.12, 2.24, 534, 123, 105

(56) References Cited

U.S. PATENT DOCUMENTS

| | | | |
|---|---|---|---|
| 5,246,576 A | * | 9/1993 | Leader et al. ............... 427/125 |
| 5,411,544 A | * | 5/1995 | Mar et al. .................... 607/122 |
| 5,433,742 A | | 7/1995 | Willis |
| 5,888,577 A | | 3/1999 | Griffin, III et al. |
| 6,032,061 A | * | 2/2000 | Koblish .................. 607/116 X |
| 6,169,916 B1 | * | 1/2001 | West ....................... 607/122 X |

* cited by examiner

*Primary Examiner*—Kevin Lee
(74) *Attorney, Agent, or Firm*—Norman E. Lehrer

(57) ABSTRACT

A process for manufacturing a flexible electrode catheter is disclosed. The process involves coating the catheter with an adhesive without affecting the integrity of the polymer substrate of the catheter. The process includes the steps of corona plasma treating a catheter, coating the catheter with an adhesive, baking the adhesive on the catheter, creating radial indents, and removing portions of the coating from the indented areas so that conduction between the different electrodes is broken. Portholes are then punched into the indented conductive areas and magnetic wires are inserted through the catheter and wrapped around the indented conductive areas. A small amount of formulated silver paint is then placed around the coiled magnetic wires. The entire indent, which includes the coiled wire and the area where the coating was removed, is then filled in radially with an adhesive coating.

2 Claims, 3 Drawing Sheets

FLEXIBLE ELECTRODE CATHETER AND PROCESS FOR MANUFACTURING THE SAME

CROSS REFERENCE TO RELATED APPLICATION

This application claims the benefit of U.S. Provisional Patent Application Ser. No. 60/168,905, filed Dec. 3, 1999.

BACKGROUND OF THE INVENTION

The present invention is directed toward a flexible electrode catheter and more particularly, toward a process which will provide an extremely flexible, versatile, and conductive coating for electrophysiology catheters.

Currently, the electrophysiology industry uses stainless steel, platinum, or gold as materials for the electrodes that transmit electric signals between the catheter and cardiac tissue. There are several disadvantages in using such rigid metal electrode bands. For one, because of the electrodes' inflexibility, metal electrodes can significantly affect the overall flexibility of the catheter by constraining the electrode lengths and spacing between individual electrode bands. Also, the methods used to fix the metal electrodes to the catheter are usually time-consuming and can damage the catheter in the process.

U.S. Pat. No. 5,433,742 to Willis discloses electrode bands which are applied to the exterior surface of a cardiac catheter. The bands may be sprayed onto the catheter. This patent, however, does not provide electrodes with the flexibility necessary for electrophysiology catheters.

SUMMARY OF THE INVENTION

The present invention is designed to overcome the deficiencies of the prior art discussed above. It is an object of the present invention to provide a flexible electrode catheter.

It is another object of the present invention to provide a manufacturing process which provides a flexible, versatile, and conductive coating for electrophysiology catheters.

It is a further object of the present invention to provide a coating for a catheter which may be applied to the catheter via atomization spraying without affecting the integrity of the polymer substrate of the catheter.

In accordance with the illustrative embodiments demonstrating features and advantages of the present invention, there is provided a process for manufacturing a conductive adhesive band electrode that is flexible and can be applied to a catheter via atomization spraying. The process includes the steps of corona plasma treating a catheter, coating the catheter with an adhesive, baking the adhesive on the catheter, creating radial indents on the coated surface of the catheter, removing portions of the coated surface from the indented areas so that conduction between the different electrodes is broken. Portholes are then punched into the catheter and magnetic wires are inserted within the catheter and wrapped around the indented conductive areas. A small amount of formulated silver paint is then placed around the areas of coiled magnetic wire. The entire indent, which includes the coiled wire and the area where the coating was removed, is then filled in radially with an adhesive coating.

Other objects, features, and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

DETAILED DESCRIPTION OF THE PREFERRED EMBODIMENT

Figure 9:
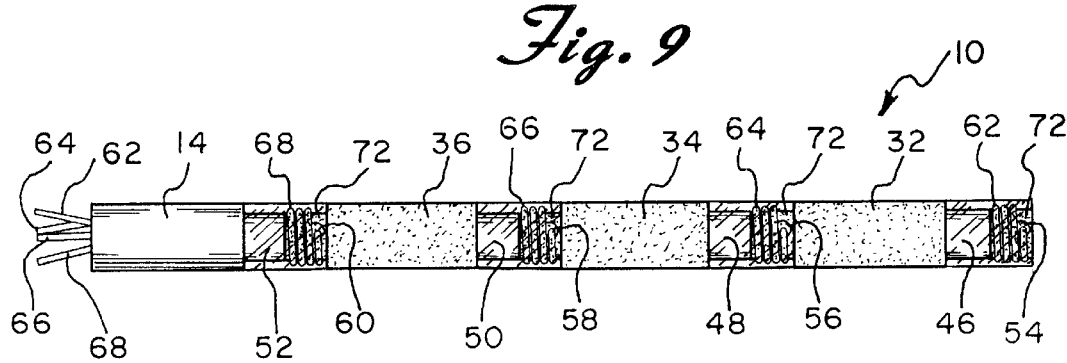
FIG. 9 illustrates the step of filling the indented areas with a polymeric material.

Referring to the drawings in detail wherein like reference numerals have been used throughout the various figures to designate like elements, there is shown in FIG. 9 a flexible electrode catheter constructed in accordance with the principles of the present manufacturing process and designated generally as 10.

Figure 1:
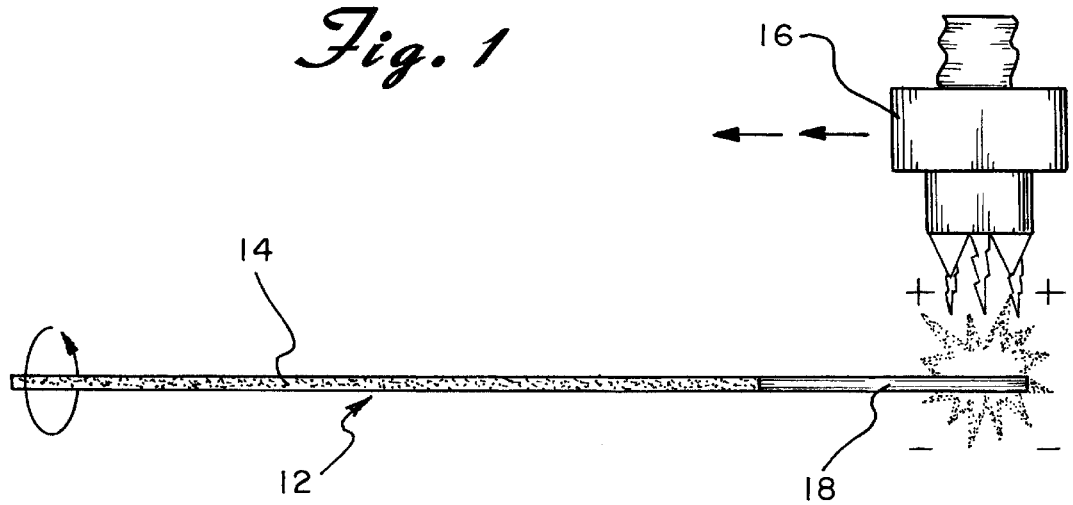
FIG. 1 illustrates the step of corona plasma treating an exposed surface of a catheter tube of the present method.

The flexible electrode manufacturing process essentially includes first providing a plastic catheter tube 12 which is cleaned with an alcohol swab and is then masked with a high temperature masking tape. However, only an approximately one-inch length 14 is required to be masked. The length 14 separates the area on the catheter tube 12 where the electrode band will be formed from the rest of the catheter. The catheter tube 12 is then mounted into a computer automated processing machine 16 that is designed to corona plasma treat the exposed surface or portion 18 of the tube 12. (See FIG. 1.)

Figure 2:
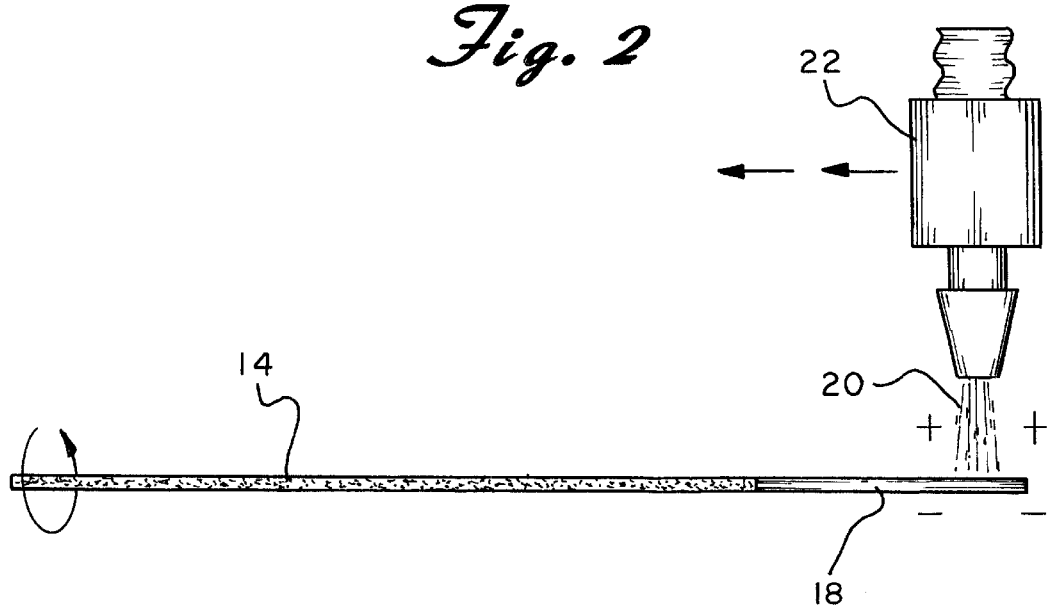
FIG. 2 illustrates the step of applying an adhesive coating to the exposed surface of the catheter tube.
Figure 3:
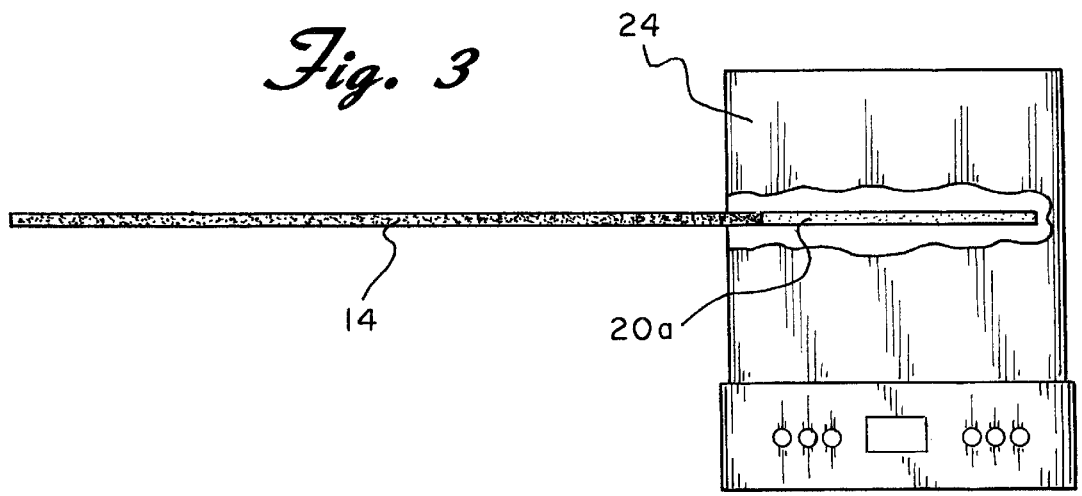
FIG. 3 illustrates the step of curing the adhesive coating on the catheter tube.

Once the exposed surface 18 has been treated, a conductive adhesive coating 20 is applied to the exposed portion 18 of the tube 12 via air atomizing as the tube 12 is rotated. The coating 20 has a formulation of approximately 75 weight % conductive ink, 1.75 weight % polyrethane, and 23.25 weight % dimethyacetamide. The adhesive coating 20 is applied to the exposed portion 18 of the tube 12 via a precision viscous spray system which is controlled by a high pressure micro-atomization microprocessor 22. (See FIG. 2.) The coating 20 may be approximately 0.0005 inches to approximately 0.0010 inches thick. The coating 20 is then baked onto the catheter tube 12 at a temperature of approximately 240° F. The curing process may take place within a microprocessor controlled curing oven 24. (See FIG. 3.) The exposed surface 18 is now a cured conductive adhesive band or surface 20a.

Figure 4:
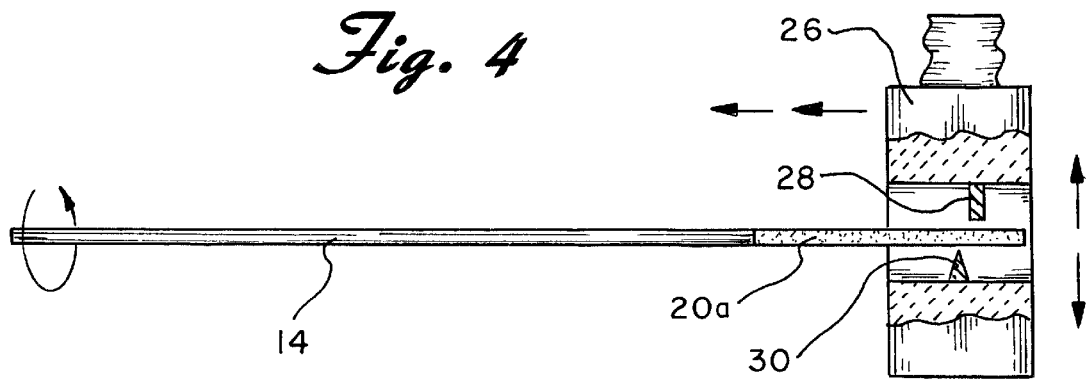
FIG. 4 illustrates the step of placing radial indents within the coated surface and removing portions of the coated surface from the indented areas of the catheter tube.
Figure 5:
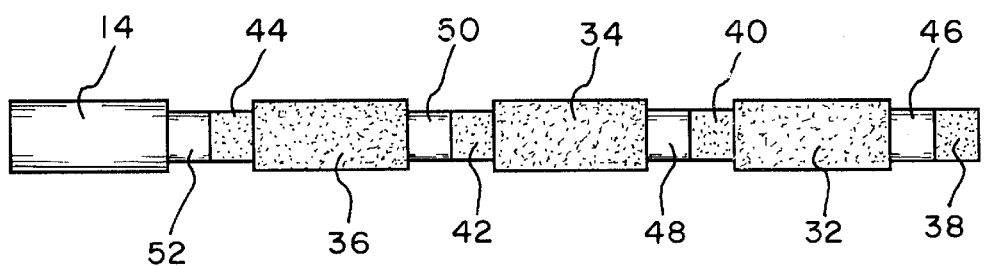
FIG. 5 illustrates the catheter tube after radial indents have been placed on the coated surface and portions of the coated surface have been removed from the indented areas.

The catheter tube 12 is then removed from the oven 24 and the masking tape is removed from the length 14 of the catheter tube 12. (Alternatively, the masking tape may be removed prior to the curing step.) The catheter tube 12 is placed into another computer automated process machine 26 which may be a microprocessor controlled X-Y-Z Servo Motor Driver Linear Slide System. The machine 26 has a grooving tool 28 and a coating removal tool 30. The grooving tool 28 is designed to place radial indents or grooves into the coated surface 20a. The removal tool 30 is designed to scratch or cut the conductive material from an area within each of the indented areas with a tolerance of approximately plus or minus 0.1 mm. Both grooving and removing operations take place as the tube 12 is rotated. (See FIG. 4.) The purpose of removing the coating at designated areas is to break the conduction between the electrodes. For example, FIG. 5 illustrates the coated portion 20a of the catheter tube 12 after the grooving tool 28 and removal tool 30 have been applied thereto. That is, three electrodes 32, 34, and 36 are shown which are separated from each other by four indented areas. Within each of the indented areas is an area 38, 40, 42, and 44 that is coated and an area 46, 48, 50, and 52 where the coating has been removed. It should be realized that three electrodes with four indented areas have been shown by way of example only and that any desired number of electrodes separated by indented areas may be formed.

Figure 6:
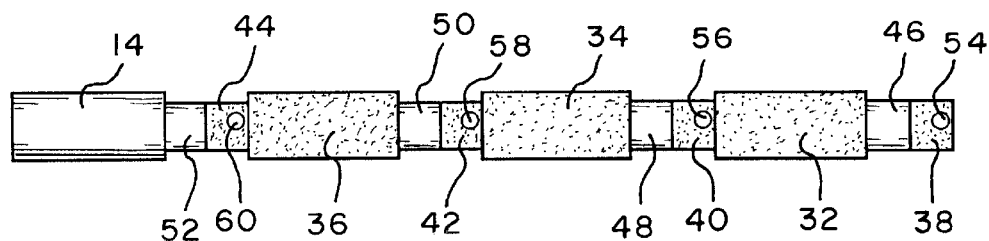
FIG. 6 illustrates the step of punching portholes within the catheter tube.
Figure 7:
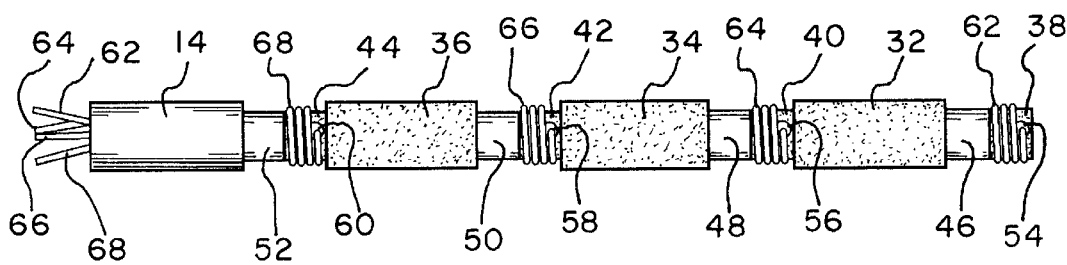
FIG. 7 illustrates the step of wrapping a conductor wire around each indented conductive area of the catheter tube.

After the catheter tube 12 has removed from the machine 26, portholes 54, 56, 58, and 60 are punched within each coated indented area 38, 40, 42, and 44, respectively. (See FIG. 6.) Magnetic wires 62, 64, 66, and 68 are then inserted through the tube 12 so that each wire extends through a different porthole. For example, wires 62, 64, 66, and 68 extend through portholes 54, 56, 58, and 60, respectively. The wires 54, 56, 58, and 60 are then wrapped around their respective indented conductive areas 38, 40, 42, and 44. (See FIG. 7.) Because the wires are placed within the indented areas, the outer surface of the catheter tube 12 will not have intermittent bulges. That is, the entire outer surface will be uniform. Each of the wires may be covered with a plastic material or the like so that the wires remain electrically isolated from each other as they run through the tube. The plastic material may be removed from the ends of the wires protruding from the portholes and wrapped around the conductive areas so as to be in contact with the conductive areas.

Figure 8:
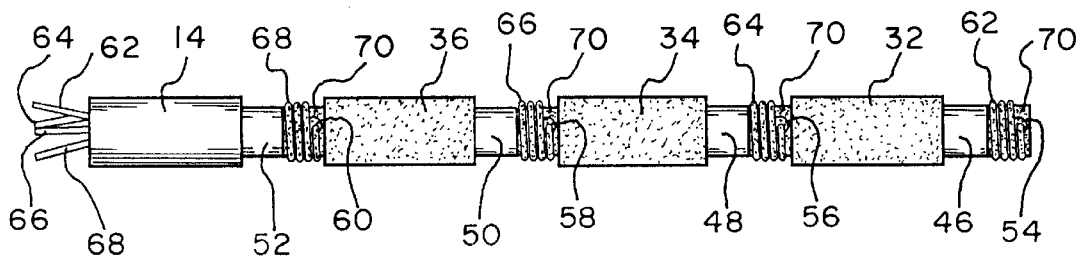
FIG. 8 illustrates the step of applying a coating over the conductor wires that are wrapped around the catheter tube.

A small amount of a conductive adhesive coating 70, such as formulated silver paint, is then placed around the coiled magnetic wires 62, 64, 66, and 68 via automated fluid dispensing equipment. This permits the magnetic wires 62, 64, 66, and 68 to be in intimate contact with their respective indented coated areas. (See FIG. 8.) Finally, the entire indented area, that is, the coiled wire and the area where the coating was removed, is then filled in radially with a self-leveling UV cured, nontransparent, polymeric adhesive 72 via EFD equipment. This adhesive insulates the electrodes and hides all underlying markings and wiring to give the catheter tube a finished, overall neat and uniform appearance. (See FIG. 9.)

The present invention provides several important advantages over the prior art. For example, the coating of the present invention is extremely flexible and possesses flexibility equal to or greater than the polymer substrate. Also, the coating is highly conductive, attaining its conductive properties from silver suspended in a polymer solution. Further, the coating is able to adhere to the most common polymers used in the electrophysiology industry without any alteration of the coating's chemical formulation.

The coating of the present invention dries quickly at a slightly elevated temperature without affecting the integrity of the polymer substrate. Animal studies have shown that the coating is able to withstand indwelling times of up to ten hours in the bloodstream without coating or conductive degradation. Other laboratory tests have shown that the coating can maintain its integrity after being immersed in a saline bath at 37° C. for 72 hours. The coating has also been proven to be biocompatible and can be sterilized without any complications. Electrode shock tests have also been performed where the coating was shocked with 50-Joule bursts over 35 times without any apparent damage to the flexible electrodes. The coating of the present invention has a higher conductivity than the prior art materials and does not affect the flexibility of the catheter.

The present invention may be embodied in other specific forms without departing from the spirit or essential attributes thereof and accordingly reference should be made to the appended claims rather than to the foregoing specification as indicating the scope of the invention.

We claim:

1. A method for forming an electrophysiology catheter with at least one electrode on the outer surface thereof comprising the steps of:

providing a catheter body having an elongated flexible tubular member with an outer surface having a proximal end and a distal end;

forming a coating of an electrically conductive material on said outer surface of said tubular member;

forming a radial groove of predetermined axial length in said outer surface in the area within the coated area while maintaining the electrical conductivity of said conductive material;

removing at least one portion of said coating within said groove so that at least two coated portions result that are electrically insulated from one another;

forming a port hole in said groove in the area of said conductive material to create communication between the interior and exterior of said tubular member;

extending an elongated flexible wire through said tubular member from said proximal end and out of said port hole;

wrapping said wire around said coating within said groove, and filling said groove with an adhesive filler material to form a smooth substantially continuous outer surface on said catheter.

2. An electrophysiology catheter with at least one electrode on the outer surface thereof comprising:

a catheter body having an elongated flexible tubular member with an outer surface having a proximal end and a distal end;

an electrode in the form of a coating of an electrically conductive material on at least a portion of said outer surface of said tubular member;

a radial groove of predetermined axial length in said outer surface, a portion of the surface of said groove being coated with said electrically conductive material and being in electrical contact with said electrode, another portion of said surface of said groove being electrically insulated from said electrode;

a port hole in said groove in the area of said conductive material creating communication between the interior and exterior of said tubular member;

an elongated flexible wire extending through said tubular member from said proximal end and out of said port hole and having its end wrapped around said coating within said groove, and an adhesive filler material filling said groove to form a smooth substantially continuous outer surface on said catheter.

* * * * *